United States Patent
Horlitz et al.

[11] Patent Number: 5,597,306
[45] Date of Patent: Jan. 28, 1997

[54] METHOD FOR SEPARABLE ATTACHMENT OF AN EPITHESIS TO A BONE, AND EPITHESIS WITH A FIXING DEVICE BY MEANS OF WHICH THIS METHOD CAN BE APPLIED

[75] Inventors: Sieglinde Horlitz, Wilhelm-Busch-Str. 39,, D-41541 Dormagen; Andy Ovist, Koln-Rodenkirchen, both of Germany

[73] Assignee: Sieglinde Horlitz, Dormagen, Germany

[21] Appl. No.: 193,142

[22] PCT Filed: Jul. 24, 1992

[86] PCT No.: PCT/DE92/00597

§ 371 Date: Aug. 22, 1994

§ 102(e) Date: Aug. 22, 1994

[87] PCT Pub. No.: WO93/03684

PCT Pub. Date: Mar. 4, 1993

[30] Foreign Application Priority Data

Aug. 13, 1991 [DE] Germany ............... 41 26 735.4

[51] Int. Cl.⁶ ............... A61C 8/00; A61C 13/24
[52] U.S. Cl. ............... 433/173; 433/174; 433/184
[58] Field of Search ............... 433/172, 173, 433/174, 175, 176, 184, 188

[56] References Cited

U.S. PATENT DOCUMENTS

| | | | |
|---|---|---|---|
| 4,382,791 | 5/1983 | Misch | 433/172 |
| 4,488,874 | 12/1984 | Soifer | 433/173 |
| 4,518,357 | 5/1985 | Brinkmann et al. | 433/173 |
| 4,547,156 | 10/1985 | Hader | 433/172 |
| 4,856,994 | 8/1989 | Lazzara et al. | 433/173 |
| 5,194,000 | 3/1993 | Dury | 433/173 |
| 5,211,561 | 5/1993 | Graub | 433/172 X |
| 5,234,341 | 8/1993 | Johansen | 433/172 |

*Primary Examiner*—Nicholas D. Lucchesi
*Attorney, Agent, or Firm*—Michael J. Kline; Noland J. Cheung; Carol I. Bordas

[57] ABSTRACT

A method and apparatus for separable attachment of an epithesis to a bone. Osseointegrated fixtures with internal threads are implanted into the bone with said fixtures being accessible from the outside. Removable screws, each with a head protruding outwards, are inserted into the fixture to enable an epithesis, manufactured from soft elastic material, to be fixed upon the head.

10 Claims, 2 Drawing Sheets

5,597,306

METHOD FOR SEPARABLE ATTACHMENT OF AN EPITHESIS TO A BONE, AND EPITHESIS WITH A FIXING DEVICE BY MEANS OF WHICH THIS METHOD CAN BE APPLIED

FIELD OF THE INVENTION

The invention relates to a method for separable attachment of an epithesis to a bone, in which osseointegrated fixtures with internal threads are implanted in the bone, said fixtures being accessible from outside and having inserted in them removable screws with a head protruding outwards and serving to fix an epithesis manufactured from soft elastic material, and also to an epithesis with a fixing device by means of which this method can be applied.

BACKGROUND OF THE INVENTION

[In accordance with the method stated above, which] It is known, for example, from the U.S. journal "The International Journal of Oral & Maxillofacial Implants", Volume 1, No. 1, 1986, to attach epithesis, i.e. special prostheses, [are attached] separably to bone tissue, in particular for craniofacial reconstruction. Reference is also made to U.S. Pat. Nos. 4,330,891 and 4,498,461. The method is based on the observation that when titanium fixtures are implanted in bone tissue, bone tissue grows around the[m] fixtures without formation of an intermediate layer, and the fixtures [they] can thereby be embedded such that other components can in turn be fixed to the fixtures [them].

According to prior art, screws are screwed into the osseointegrated fixtures and the heads of the individual screws screwed in [in] this manner are connected together by means of a wire structure. This wire structure is located at a distance of a few millimeters from the skin and is therefore visible from the outside. In an early design, the epithesis proper is clipped onto the wire structure, and to this end the epithesis, which is manufactured largely from silicone rubber, has plastic clips embedded in the silicone material and formed according to the path of the wire structure. These clips are pressed onto the wire structure, thereby holding the epithesis to the wire structure. In another design, the wire structure includes permanent magnets, [and] the paired attracting magnets are embedded at the corresponding points of the epithesis proper, thereby providing magnetic retention of the entire epithesis to the wire structure.

This previously known method has a number of disadvantages. Manufacture of the wire structure is very labo[u]r-intensive. The wire structure also obstructs cleaning of the skin or impedes cleaning if the wire structure is of removable design. The wire structure is irritating to the patient; when the epithesis is removed for washing or showering, a rigid structure remains in place which is obstructive and which the patient perceives as alien. Moreover, manufacture of the epithesis is also labo[u]r-intensive, since the appropriate corresponding components, i.e. clips or magnets, must be embedded in the silicone rubber material. The rubber material, however, bonds neither to the magnets nor to the clips, and special measures are therefore also necessary in this regard. A genuinely reliable, long-term embedding of the corresponding components in the silicone material is, however, not achieved in this way.

Taking as a basis the method described above, the object of the invention is to improve this method and to provide an epithesis with a fixing device for application of this [the] method to the effect that the fixing device is substantially simplified, that the manufacture of the fixing device and therefore [of] the epithesis is likewise substantially simplified, that fitting and removal of the epithesis is simplified for the patient, at the same time guaranteeing a sufficiently secure connection of the epithesis, which cannot always be achieved with magnetic attachment, and that the need for a wire structure is obviated.

SUMMARY OF THE INVENTION

With regard to the method, this object is achieved by the employment of screws having undercut heads, in particular mushroom-shaped heads, and by the provision in the epithesis of recesses corresponding to the screw heads, in which the heads engage in press-stud fashion.

This solution has the decisive advantage that the epithesis proper can be manufactured from silicone rubber or other rubber-like materials without the need for a clip or a magnet to be embedded. Manufacture of the epithesis is simplified as a result, and the problems associated with bonding the silicone rubber material to a clip or magnet do not arise. There is no need for a wire structure on the patient; rather, when the epithesis is removed, only a number of mushroom-shaped heads project from the region of the skin onto which the epithesis is placed. The screws present no hindrance during washing or showering, and the surrounding skin can be cleaned without difficulty. Overall, a very secure connection is attained which can be further improved in each case by adaptation of the dimension of the undercut (undercut ratio) to the elasticity of the silicone rubber employed.

From the physician's point of view, manufacture of the epithesis with the fixing device is significantly simplified, [manufacture is simplified in] particularly [in addition] if a silicone rubber or other rubber-like material which vulcanizes at room temperature is employed.

With regard to the device, the object is achieved by the epithesis having a number of recesses formed in the soft elastic material which widen inwards, and by the fixing device having screws provided with an undercut and having heads, particularly mushroom-shaped heads, the shape of which is matched to the recesses. The advantages already described are attained by this embodiment of the device.

A suction hole on the free end of the heads has proven to be particularly advantageous. The suction hole is a blind hole, for example of conical, semispherical or truncated cone form. When, during manufacture of the epithesis, the heads of the screws are embedded in the silicone rubber compound before it is vulcanized, the suction holes are filled, for example, with wax, such that no rubber compound can flow into them. [They are filled for example, with wax.] Following full curing and removal from the mo[u]ld, the suction holes are cleared again. [They] These suction holes subsequently generate additional adhesion between the rubber material of the epithesis and the heads, in the same way that this occurs with suction cups.

Preferably, the heads are turned parts, thus having [they have] no edges or corners. Manufacture is simplified as a result, and no problems arise during alignment of the heads in the model used for manufacture of the epithesis and during alignment in the osseointegrated fixtures.

Preferably, the undercut is at least two to one, and preferably four to one or more. An undercut ratio of two to one, for example, is taken to mean that the diameter of the widest point of the head as seen from the free end is twice as large as the smallest diameter in a subsequent neck. The silicone rubber material possesses particularly high extensibility, with the result that undercuts with a high undercut ratio can be realiz[s]ed without the danger of tearing of the rubber material when the epithesis is removed or pressed in place.

The use of silicone rubber which vulcanizes at room temperature further simplifies manufacture of the epithesis; reference to this having [has] already been made. A rubber of this type is available from Wacker and bears the designation "Wacker-Silicon-Kautschuk RTV-M 539". This is a brushable, stable silicone rubber which cross-links by condensation, which possesses exceptional resistance to tearing and tear-off propagation, and which is soft and extremely extensible when vulcanized. The consistency is soft-pasty. Finally, the vulcanized rubber is non-toxic and is fatigue resisting.

BRIEF DESCRIPTION OF THE DRAWINGS

Embodiments of the invention, which serve in particular to explain the method according to the invention, are described below. They are not to be regarded as restrictive. Further advantages and features of the invention emerge from these examples. The drawings show[s]n in.

DETAILED DESCRIPTION OF THE PRESENTLY PREFERRED EMBODIMENTS

Figure 1:
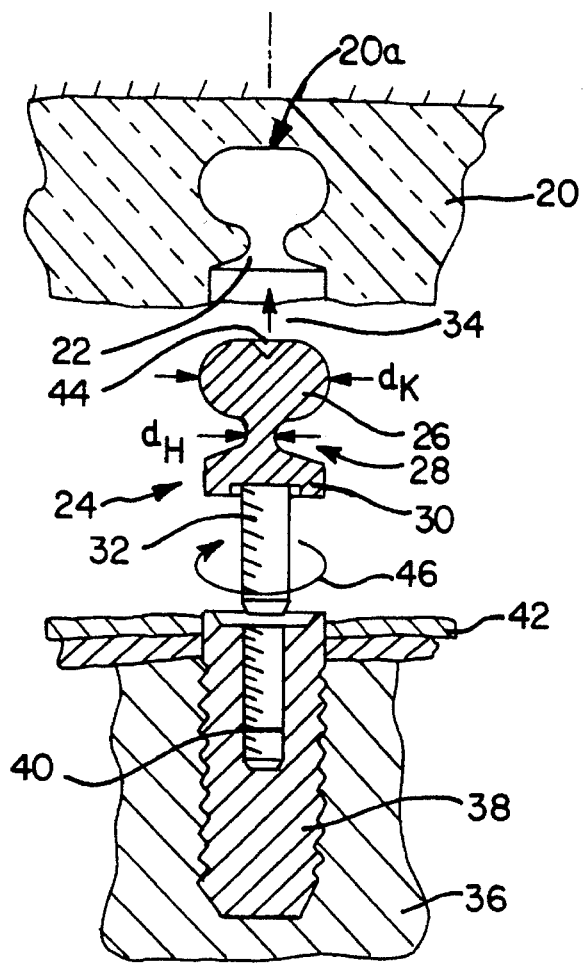
FIG. 1 A sectional view (in the form of an assembly drawing) through a fixture anchored in the bone tissue, with internal thread; through a screw (suction retention knob) and (above) through an epithesis.

At the top of FIG. 1, which represents an assembly drawing, part of an epithesis 20 is shown. It is manufactured from an RTV-M 539 silicone rubber produced by Wacker and pigmented to the colo[u]r of a patient's skin. On its upward-facing surface 20a in FIG. 1, it has a skin structure in which individual hairs are imbedded. The epithesis 20 may be an ear or a nose, etc.

The epithesis 20 is retained by means of a number of fixing devices, which are dealt with in detail below. FIG. 1 shows only one fixing device, but at least two and preferably several fixing devices are provided, being preferably of identical design.

One recess 22 per fixing device is provided on the underside of the epithesis 20 itself. The recess 22 is undercut, i.e. widens out inwards from an opening.

A screw, generally 24 is located beneath the depicted part of [the] an epithesis 20. The screw 24 is preferably a single-piece item comprising a head 26, a neck 28, a collar 30 and a threaded portion 32. With the exception of the threaded portion 32, the screw 24 is preferably a turned part. The recess 22 in the epithesis 20 corresponds in form to the shape of the head 26, neck 28 and collar 30. Pressure in the direction of the arrow 34 causes these items 26, 28, and [to] 30 to snap into the recess 22, thereby ensuring that the screw 24 and epithesis 20 [they] remain connected to each other.

The head 26 has a greatest outside diameter $d_K$, which is termed the head diameter. The neck 28 has a smallest diameter $d_H$, termed the neck diameter. The ratio of these two diameters is termed the undercut ratio; in the embodiment as per FIG. 1, this undercut ratio is $d_K/d_H=3.2$. The undercut ratio is matched to the hardness and the extensibility of the vulcanized silicone rubber. In the case of harder adjusted types of vulcanized rubber, a smaller undercut ratio is selected, e.g. 2. In the case of softer adjusted types of vulcanized rubber, the undercut ratio is increased, and may then, for example, be 5.

Finally, the implanted part of the fixing device is located beneath the screw 24, as illustrated in FIG. 1. A recess is created in a bone 36, and a fixture 38 with inside thread 40 is inserted into the recess, for example by screwing the fixture 38 into the bone 36, the fixture 38 having outside threads 39 for this purpose. Towards the outside of the implanted fixture 38 there is [are] an intermediate layer 41 and a skin layer 42 above the bone and to the side of the fixture 38, allowing easy external access [from outside] to the fixture 38 and in particular to its inside thread 40 at any time. The inside thread 40 is matched to the threaded portion 32 of the screw 24. The osseointegrated part of the fixing device is known; reference is made herein to the prior art, incorporated by reference herein, and a precise description is therefore unnecessary.

The [S]screw 24 and fixture 38 are preferably manufactured of the same material, e.g. titanium or another metal. Plastics or ceramic materials may, however, also be used.

A suction hole 44 is located at the free end of the head 26. This suction hole 44 is closed [up] during the preparation of [for] the duplicate mo[u]ld of the screw 24 used to [for] manufacture [of] the recess 22 of the epithesis 20; recess 22 therefore has no projection corresponding to the suction hole 44. As a result, a volume of air at partial vacuum is left in the suction hole 44 when the head 26 is inserted into the recess 22. This reinforces the adhesive effect.

The collar 30 need not necessarily be present. As can be seen from FIG. 1, it has the same outside diameter at [as] the end of the fixture 38 projecting above the skin layer 42, thereby providing a clean termination at this point.

For the purpose of assembly, the screw 24 is first screwed into the inside thread 40 in the direction of the arrow 46 until the underside of the collar 30 rests on the upper side of the fixture 38. The screw 24 can be manually screwed into the fixture 38 [manually]. The epithesis 20 is then pressed on by the application of a certain amount of pressure in the same way that a press-stud is fastened, until the head 26 snaps into its associated recess 22. The same procedure is followed for the adjacent fixings. The epithesis 20 is then attached[.] and [It] can be released from screw 24 again by being pulled up and off.

Figure 2:
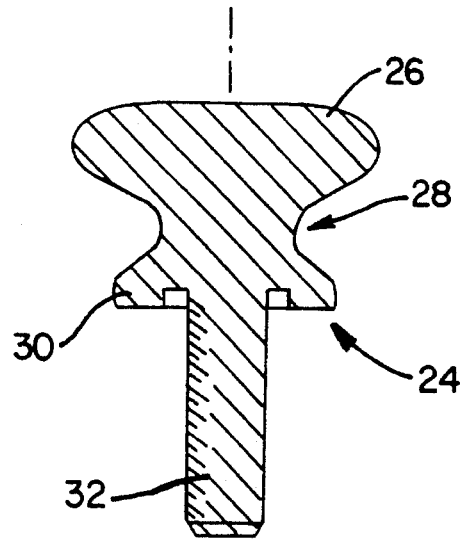
FIG. 2 A sectional view through a screw (retention knob) as per FIG. 1, but of different design.

FIG. 2 shows a screw 24 without a suction hole 44 and resembling a bollard in form. The mushroom shape of the head 26 can be seen clearly in this case. The diameter of the head is greater than the outside diameter of the collar 30. A lower overall height is achieved than with the screw as per FIG. 1.

Figure 3:
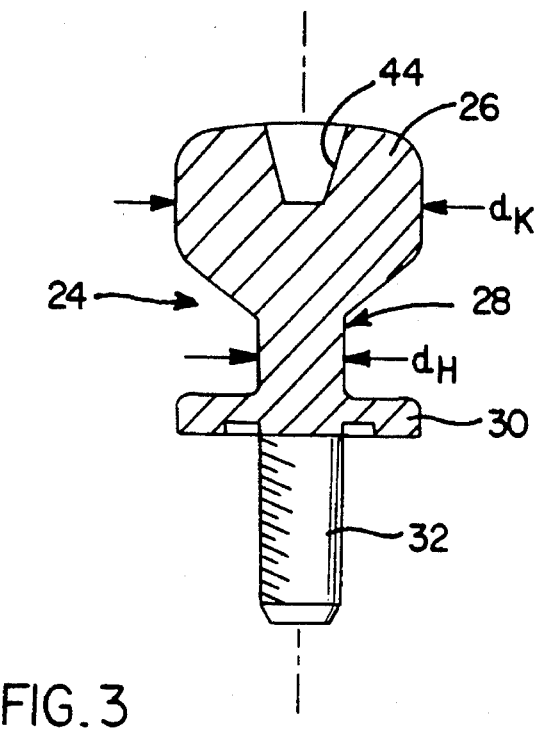
FIG. 3 A sectional view through a suction retention knob similar to FIG. 1.

FIG. 3 shows a further embodiment of a screw 24. The undercut ratio $d_K/d_H$ is approximately 3 in this instance. The head 26 has a suction hole 44 in the shape of a truncated cone. The neck 28 is longer than in the case of the embodiments described previously, resulting in greater forces being required for removal and correspondingly greater forces being required for fitting. Collar 30 has a very low height.

Figure 4:
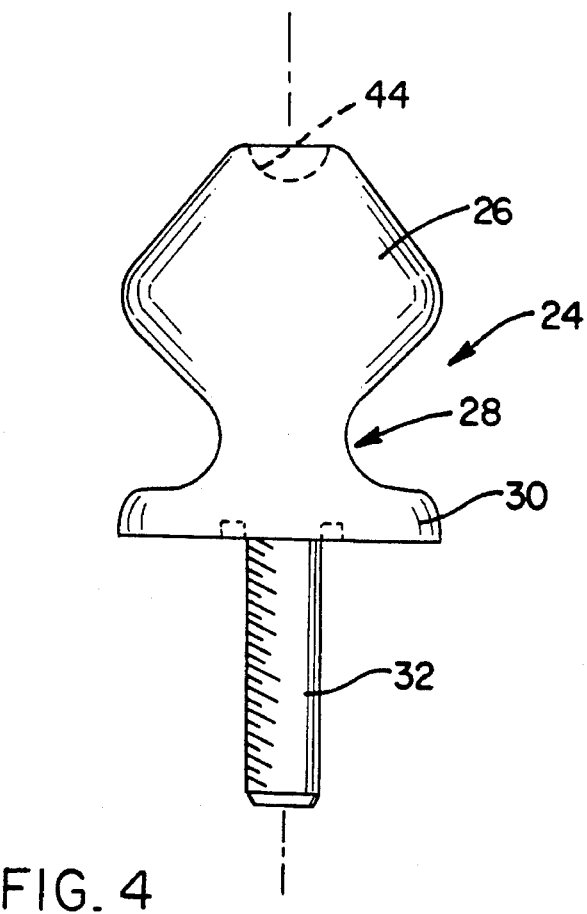
FIG. 4 A side view of a suction retention knob.

Finally, FIG. 4 shows an embodiment of a screw 24 in which the free end of the head 26, which once again has a—in this case, semispherical—suction hole 44, has a certain taper or truncated cone form. The objective here is to enable the head 26 to locate the recess 22 without difficulty when the epithesis 20 is placed in position, without the [centre] center lines (and rotational axes) of recess 22 and head 26 having to coincide exactly. Rather, the head 26 in the embodiment per FIG. 4 centers [centres] itself owing to the upward taper of its form.

Although the invention has been described in detail in the foregoing for the purpose of illustration, it is to be understood that such detail is solely for that purpose and that variations can be made therein by those skilled in the art without departing from the spirit and scope of the invention as defined by the claims.

We claim:

1. A method for separable attachment of an epithesis (20) to a bone (36), in which at least one fixture (38) is implanted in the bone (36), the fixture (38) being externally accessible, comprising:

a. implanting said at least one fixture (38) into said bone (36);

b. providing at least one fastening means (24) for attaching said epithesis (20) to said bone (36), each said fastening means (24) including an outwardly protruding head (26), and further including an undercut;

c. fastening one said fastening means (24) to each said fixture (38);

d. providing a recess in said epithesis (20) for each said fastening means (24), each said recess having a shape corresponding to the shape of said outwardly protruding head (26) and said undercut; and e. fastening said epithesis (20) to said bone (36) by pressing each said fastening means (24) into each said recess.

2. A method for separable attachment of an epithesis comprising a soft, elastic material to a bone comprising the steps of:

(a) implanting at least one fixture having a tapped region with internal threads into said bone;

(b) providing one screw for each said fixture and removably inserting a first end of one said screw into the tapped region of each said fixture, each said fixture being accessible from the outside of said tapped region; and (c) attaching said epithesis to a second end of each said screw, said epithesis having at least one recess provided in said soft, elastic material, wherein each said recess widens inwardly, each said second end of each said screw comprising an enlarged head portion having a top portion and an undercut to engage with each said recess of said epithesis, each said head having a suction hole located at said top portion of said head.

3. A method for separable attachment of an epithesis comprising a soft, elastic material to a bone comprising the following steps:

(a) implanting at least one fixture having a tapped region with internal threads into said bone;

(b) providing one screw for each said fixture and removably inserting a first end of one said screw into the tapped region of each said fixture, each said fixture being accessible from the outside of said tapped region; and (c) attaching said epithesis to a second end of each said screw, said epithesis having at least one recess provided in said soft, elastic material, wherein each said recess widens inwardly, said second end of each said screw comprising an enlarged head portion having an undercut to engage with each said recess of said epithesis.

4. A method according to claim 3, wherein each said head of said second end of said screw is mushroom-shaped.

5. A method according to claim 4, wherein each said mushroom-shaped head comprises a top portion which includes a suction hole.

6. A method according to claim 4, wherein each said head of said screw tapers from a diameter $d_k$ to a diameter $d_h$ of a neck, said ratio of $d_k$ to $d_h$ is at least two.

7. A method according to claim 6, wherein the ratio of $d_k$ to $d_h$ is at least three.

8. A method according to claim 3, wherein each said head comprises turned parts.

9. A method according to claim 3, wherein said epithesis is manufactured from a silicone rubber which vulcanizes at room temperature.

10. An apparatus for separable attachment of an epithesis to a bone, comprising at least one screw and at least one fixture, wherein each said fixture is adapted to be implanted in said bone, each said fixture having internal threads; each said screw having a first and second end, said first end of each said screw being removably insertable into each said fixture, said second end of each said screw comprising a head having an undercut; said head of said second end of each said screw comprising a mushroom-shaped head; said mushroom-shaped head comprises a top portion which includes a suction hole; said epithesis comprising a soft, elastic material and having at least one recess which widens inwardly to receive said second end of each said screw.

* * * * *